United States Patent [19]

Kranys

[11] Patent Number: 5,207,656
[45] Date of Patent: May 4, 1993

[54] MEDICAL INSTRUMENT VALVE HAVING FOAM PARTITION MEMBER

[75] Inventor: Rudy J. Kranys, Coconut Grove, Fla.

[73] Assignee: Cordis Corporation, Miami Lakes, Fla.

[21] Appl. No.: 510,946

[22] Filed: Apr. 19, 1990

[51] Int. Cl.⁵ ............................................. A61M 5/00
[52] U.S. Cl. ...................................... 604/256; 604/167
[58] Field of Search ............... 604/167, 169, 256, 237, 604/265

[56] References Cited

U.S. PATENT DOCUMENTS

| | | | |
|---|---|---|---|
| 4,000,739 | 1/1977 | Stevens | 128/244.4 |
| 4,324,239 | 4/1982 | Gordon et al. | 604/256 |
| 4,475,548 | 10/1984 | Muto | 604/167 |
| 4,610,665 | 9/1986 | Matsumoto et al. | 604/167 |
| 4,626,245 | 12/1986 | Weinstein | 604/167 |
| 4,673,393 | 6/1987 | Suzuki et al. | 604/167 |
| 4,693,257 | 9/1987 | Markham | 604/167 |
| 4,798,594 | 1/1989 | Hillstead | 604/167 |
| 4,895,346 | 1/1990 | Steigerwald | 604/167 |
| 4,895,565 | 1/1990 | Hillstead | 604/167 |
| 4,950,257 | 8/1990 | Hibbs et al. | 604/265 |

*Primary Examiner*—Paul R. Hirsch
*Assistant Examiner*—L. Thomas
*Attorney, Agent, or Firm*—Gerstman & Ellis, Ltd.

[57] ABSTRACT

A medical instrument such as a catheter introducer comprises a housing. The housing includes a valve for receiving and sealing an elongated member which penetrates the valve. The valve comprises an elastomeric partition member. By this invention, the partition member comprises a foamed elastomer material to facilitate penetration of the elongated member therethrough and sealing of the valve

10 Claims, 1 Drawing Sheet

MEDICAL INSTRUMENT VALVE HAVING FOAM PARTITION MEMBER

BACKGROUND OF THE INVENTION

Hemostasis valves are well-known, being currently used, for example, in arterial catheter introducers, used with catheters for performing percutaneous transluminal coronary angioplasty (PTCA), as well as catheters for angiographic procedures, for example where x-ray contrast fluid is inserted through a catheter into the coronary artery. The hemostasis valve is typically used to prevent the leakage of blood out of or around dilatation and other catheters which particularly enter into an artery, to prevent the reverse seepage of blood out of the patient into the operating field. Typically, hemostasis valves are conventionally positioned at the proximal ends of catheter introducers, which are used in conjunction with guide wires to facilitate the entrance of catheters into an artery or other blood vessel.

Numerous types of hemostasis valves are known. By way of example, see Stevens U.S. Pat. No. 4,000,739, Matsumoto et al. U.S. Pat. No. 4,610,655, Weinstein U.S. Pat. No. 4,626,245, and Hillstead U.S. Pat. No. 4,798,594.

In all of the previously cited patents, the hemostasis valves include an elastomeric partition of a solid, nonporous material which defines a slit through the partition, to facilitate the advancement of a catheter or guide wire through the hemostasis valve.

By this invention, a significant modification is provided to a hemostasis valve for use in a medical instrument such as a catheter introducer. Improved ease of advancement of the catheter through the hemostasis valve partition can be achieved, while good sealing against blood leakage is provided. Furthermore, with this invention it may not be necessary to provide a slit or other aperture through the elastomeric partition used in this invention, with an advancing probe such as a guide wire forming its own aperture, so that a better sealing fit is provided between the advancing probe and the partition as the probe is advanced through the hemostasis valve.

DESCRIPTION OF THE INVENTION

A medical instrument is provided, which instrument comprises a housing. The housing includes a valve for receiving and sealing an elongated member which penetrates the valve. This elongate member is, typically, a guide wire, generally followed by a catheter. The valve comprises an elastomeric partition member through which the elongated member can pass.

In accordance with this invention, the elastomeric partition member comprises a foamed elastomer material, to facilitate penetration of the elongated member therethrough and sealing of the valve. If desired, the partition member may define a reclosable aperture such as a slit to further facilitate penetration of the elongated member through the partition member. The specific design of slit may be of any of the types disclosed in the patents cited above, so that the advantages of those particular slit designs may be combined with the advantage of the foamed elastomer partition member of this invention. Alternatively, the reclosable aperture may be a single, normally closed puncture hole through the partition member, which may be stretched and expanded by an advancing, elongated member to facilitate passage through the partition member.

Alternatively, the foamed partition member of this invention may be aperture free, with an aperture being formed through the partition by an advancing guide wire or other probe, to facilitate advancement of a subsequent catheter through the foamed partition member.

The foamed elastomer material of the partition member may be an open cell foam, or, alternatively, it may be a closed cell foam. Open cell foams are generally characterized by passages that interconnect most of the cells in the foam. Alternatively, open cell foams may be so open that they exhibit in a micrograph a fibrous, lacy aspect rather than appearing to define discrete cells with walls, and such structures are deemed to be one type of open cell foam for use herein. An advantage of open cell foams is that they tend to be more compliant than closed cell foams, since the air in the cells can migrate to other cells as a probe passes through the partition member, stretching and expanding the member. Thus, the air is not compressed as in closed cell foams. In closed cell foams, the air in the cells has no way of escape, without breaking cell walls.

As a further advantage of open cell foams, they may contain desired lubricants, antithrombogenic agents, sterilizing agents, medicaments, or the like, which may pass onto the surface of the elongated member as it advances through the partition member. Thus, for example, a lubricant may facilitate the advancement of an elongated member through the partition member.

Closed cell foams give, as previously stated, a somewhat different behavior when expanded by a penetrating elongated member in that, generally, there is no escape for the air entrapped in the closed cells of the foam unless the cell walls are ruptured. Here also, materials such as lubricants, medications, and the like can be added since the cell wall properties can be designed so that cells rupture as an elongated member passes through the partition. Also, closed cell foams provide an improvement in sealing, in that blood cannot migrate through the microstructure of the closed cell foams since there is no flow path, while with open cell foams, some blood migration might take place this way. However, if the elastomer material is generally hydrophobic in nature, i.e. so that water tends to bead up on the surface of the material rather than forming a film on its surface, then blood is unlikely to migrate in significant quantities through an open cell foam partition member even though interconnected passageways exist through the member. Thus, it is generally preferred for the elastomer material to be hydrophobic in nature.

Specific foamed elastomer materials which may be used include polyurethanes, and foamed hydrocarbon elastomers such as polybutadiene, polyisoprene, or natural rubber latex. Additionally, thermoplastic foamed elastomer materials may be used, for example, Kraton elastomer, which is a material sold by Shell Chemical Company comprising a hydrocarbon elastomer block copolymer with moieties of polystyrene.

Preferably, the foamed elastomer material used in the partition member defines foam cells which have diameters of substantially 0.001 to 0.05 inch, so that the material exhibits distinct foam characteristics, but the foam cells are not so large as to significantly reduce the sealing characteristics of the partition member.

DESCRIPTION OF SPECIFIC EMBODIMENTS

Figure 1:
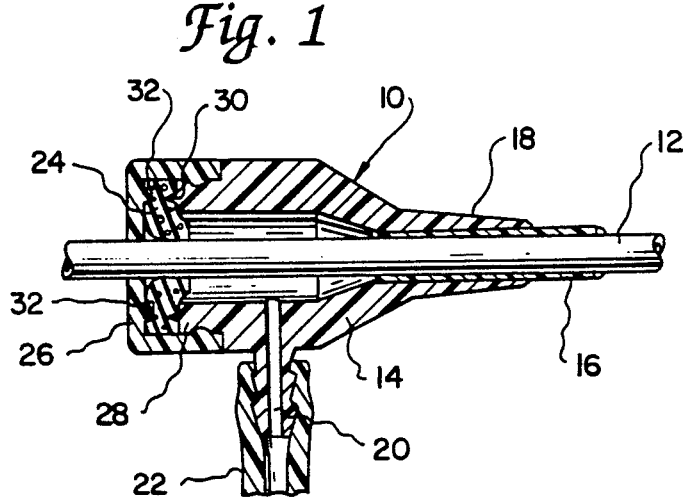
FIG. 1 is a fragmentary, longitudinal sectional view of a hemostasis valve in accordance with this invention, carried on a catheter introducer, and showing a catheter penetrating the hemostasis valve.
Figure 2:
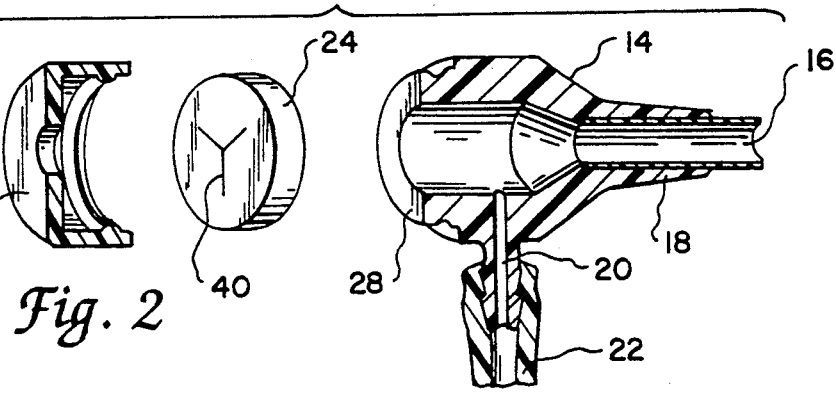
FIG. 2 is a fragmentary, exploded perspective view of the hemostasis valve of FIG. 1, with parts shown in section.

Referring to the drawings, FIGS. 1 and 2 show the proximal end of a catheter sheath introducer 10 which may be of entirely similar design to any of various known, commercially available catheter sheath introducers, except as otherwise described herein. Catheter sheath introducer 10 is adapted to receive an inner catheter 12 as shown for insertion into the vascular system of a patient. Catheter sheath introducer 10 is used to introduce the catheter into a blood vessel, while preventing blood backflow along the outside surface of the catheter during procedures in which the catheter is inserted into the vessel.

Catheter sheath introducer 10 defines outer tubular housing 14, which carries cannula portion 16 (mostly broken away) of the catheter sheath introducer 10, positioned in attached telescoping relation with tubular protrusion 18 of the housing. Side port 20 may be of conventional design, being adapted for telescoping connection with plastic tubing 22, for its conventional purpose in a catheter sheath introducer.

Housing 14 also carries a self-sealing, penetrable barrier as elastomeric partition 24. In accordance with this invention, elastomeric partition 24 is made of a foamed elastomer material, for example foamed natural rubber latex, polyurethane, silicone elastomers, fluoropolymers, or any other foamed elastomer. As previously stated, the foam cells of partition 24 may carry a lubricating oil to facilitate penetration of catheters or the like. Alternatively, the lubricating oil may be absorbed in the material of the foam itself for similar purposes.

Housing 14 may comprise casing portions 26, 28 which are sealed together in snap-fit, telescoping relation, and which peripherally capture partition 24 between them as shown. Alternatively, casing 26 may be a screw cap, for adjustable, compressive retention of the periphery of partition 24. Annular ribs 30, 32 may be provided in each casing portion to provide more positive capture of partition 24. Additionally or alternatively, partition 24 may be solvent, heat, or ultrasonically bonded to one or both of casing portions 26, 28.

As shown in FIG. 2, partition 24 may define a Y-shaped slit 40, or any other design of slit as may be desired to facilitate the penetration of a catheter or guide wire through partition 24. As taught in Hillstead U.S. Pat. No. 4,798,594, slit 40 may be rotated in helical manner as it extends through partition 40 for improved sealing characteristics.

Figure 3:
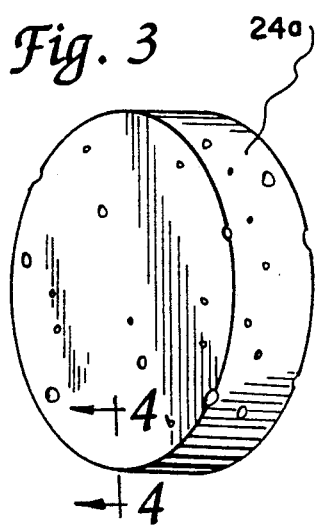
FIG. 3 is a perspective view of another embodiment of the partition member shown in FIGS. 1 and 2.

Alternatively, as shown in FIG. 3, partition 24a may be a foamed elastomer partition similar to partition 24 but without any slit. Rather, one may press a guide wire or other probe through the partition 24a, forming a slit that exactly fits the transverse dimensions of the probe. Partition 24a may be used as a substitute for partition 24 in the structure of FIGS. 1 and 2.

Figure 4:
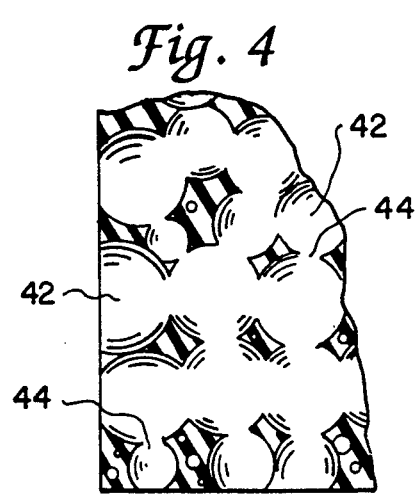
FIG. 4 is a highly magnified, fragmentary, sectional view of the foamed elastomer material of one embodiment of partition member used in this invention, taken along line 4—4 of FIG. 3.
Figure 5:
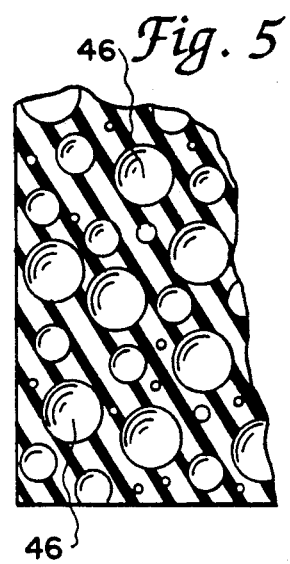
FIG. 5 is a highly magnified, fragmentary, sectional view of another embodiment of the foamed elastomer material usable in the partition member of this invention, also taken along line 4—4 of FIG. 3.

FIGS. 4 and 5 show two other aspects of possible embodiments in accordance with this invention, which may be used respectively in conjunction with the structure of FIGS. 1 and 2, containing either partition 24 or partition 24a.

FIG. 4 illustrates an open cell foam, in which the individual cells 42, which are typically generally spherical in shape, have walls that are interrupted by passageways 44 communicating with adjacent, neighbor cells. Thus, the open cell foam defines interconnecting passageways that generally extend entirely through the partition, unless it is desired to use a partition having a closed skin over one or both major surfaces, as may be desired in some circumstances.

In the embodiment of FIG. 5, a closed cell foam is shown, in which the foam cells 46 are generally closed off from each other by their walls, so that each cell, or group of cells in some cases, are entirely isolated by the walls of the elastomeric, foamed material.

As previously described, the functioning characteristics of the open cell foam and closed cell foam elastomeric partitions differ from each other, so that specific and differing characteristics of a partition may be achieved by proper selection of the elastomer material selected for use as the partition with regard to such factors as: the size, shape and distribution of the foam cells, whether the cells are of open cell or closed cell form, the dimensions of the partition, whether or not a slit or other aperture is present and the specific shape thereof, and the inherent physical properties of the elastomer material.

By this, a variety of selected, good functional characteristics may be provided for a hemostasis valve, through the use of the foamed elastomer partitions of this invention.

The above has been offered for illustrative purposes only, and is not intended to limit the scope of the invention of this application, which is as defined in the claims below.

That which is claimed is:

1. An arterial catheter introducer which comprises a cannula portion and a proximally positioned, tubular housing, said housing comprising a valve for receiving and sealing an elongated member which penetrates said valve, said valve comprising an elastomeric partition member, the improvement comprising, in combination:
   said partition member comprising a closed-cell foam; hydrophobic elastomer material, the closed cells of said foam carrying a liquid agent within said cells to facilitate penetration of said elongated member therethrough and sealing of said valve, said partition member being initially aperture-free prior to use.

2. The medical instrument of claim 1 in which said foamed elastomer material defines foam cells having diameters of substantially 0.001 to 0.05 inch.

3. A medical instrument comprising a housing, said housing comprising a valve for receiving and sealing an elongated member which penetrates said valve, said valve comprising an elastomeric partition member, the improvement comprising, in combination:

said partition member comprising a foamed elastomer material of the closed cell foam type, closed cells of said foamed elastomer material carrying a liquid agent to facilitate the use of said medical instrument.

4. The medical instrument of claim 3 in which said liquid agent is a lubricant.

5. The medical instrument of claim 3 in which said partition member defines a recloseable aperture to facilitate penetration by said elongated member.

6. The medical instrument of claim 3 in which said partition member is free of an aperture extending transversely therethrough whereby said elongated member must rupture cells of the foam as it penetrates said partition.

7. The medical instrument of claim 6 in which said elastomer material is generally hydrophobic in nature.

8. The medical instrument of claim 3 in which said foamed elastomer material defines foam cells having diameters of substantially 0.001 to 0.05 inch.

9. An arterial catheter introducer which comprises a cannula portion and a proximally positioned tubular housing, said housing comprising a valve for receiving and sealing an elongated member which penetrates said valve, said valve comprising an elastomeric partition member, the improvement comprising, in combination:

said partition member comprising a foamed, hydrophobic elastomer material, with the foamed elastomer material defining cells which carry a lubricant to facilitate the use of said catheter introducer.

10. The medical instrument of claim 9 in which said foamed elastomer material is a closed cell foam.

* * * * *